United States Patent
Wang et al.

(10) Patent No.: US 6,391,175 B1
(45) Date of Patent: May 21, 2002

(54) CARBONATE IONOPHORE WITH IMPROVED SELECTIVITY

(75) Inventors: Chengrong Wang, Hockessin, DE (US); Daniel Brown, Sacramento, CA (US)

(73) Assignee: Dade Behring Inc., Deerfield, IL (US)

( * ) Notice: Subject to any disclaimer, the term of this patent is extended or adjusted under 35 U.S.C. 154(b) by 22 days.

(21) Appl. No.: 09/716,889

(22) Filed: Nov. 21, 2000

(51) Int. Cl.[7] .................. G01N 27/40; C07C 225/00
(52) U.S. Cl. .................. 204/418; 564/161; 564/164; 564/169; 564/183
(58) Field of Search .................. 204/418; 564/161, 564/164, 169, 183; 568/335

(56) References Cited

U.S. PATENT DOCUMENTS

| | | |
|---|---|---|
| 3,723,281 A | 3/1973 | Wise |
| 4,272,328 A | 6/1981 | Kim et al. |
| 4,810,351 A | 3/1989 | Chapoteau et al. ......... 204/418 |
| H745 H | 2/1990 | Ishizuka et al. ............ 204/418 |
| 4,933,048 A | 6/1990 | Lauks |
| 5,174,872 A | 12/1992 | Scott |
| 5,284,568 A | 2/1994 | Pace et al. .................. 204/403 |
| 5,522,978 A | 6/1996 | Pace .......................... 204/418 |

FOREIGN PATENT DOCUMENTS

| | | | |
|---|---|---|---|
| JP | 11-24217 | * 1/1999 | |
| WO | WO 98/38503 | 9/1998 | ......... G01N/27/333 |

OTHER PUBLICATIONS

Maj–Zurawska et al, Talanta 44, (1997), pp. 1641–1647.*
Shin et al, Journal of Electroanalytical Chemistry, 468, (1999), pp. 76–84.*
Dinten et al, Analytical Chemistry, 63, (1991), pp. 596–603.*
Behringer et al, Analytica Chimica Acta, 233, (1990), pp. 41–47.*

* cited by examiner

Primary Examiner—Robert J. Warden, Sr.
Assistant Examiner—Kaj K. Olsen
(74) Attorney, Agent, or Firm—Leland K Jordan

(57) ABSTRACT

The invention pertains to a novel ionophore having the general structure:

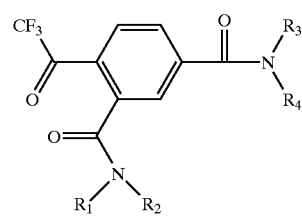

wherein $R_1$, $R_2$, $R_3$ and $R_4$ are independently straight or branched chain alkyl having 4 to 12 carbon atoms or the alkyl groups may optionally contain a cycloalkyl group having 3 to 8 carbon atoms or $R_1$ and $R_2$ or $R_3$ and $R_4$ together with N to which they are attached, can form a ring having 5 to 8 carbon atoms. This ionophore has increased selectivity for carbonate ions over other ions, especially salicylate. The invention includes membranes containing effective amounts of the novel ionophores and -sensors containing these membranes.

12 Claims, No Drawings

CARBONATE IONOPHORE WITH IMPROVED SELECTIVITY

FIELD OF THE INVENTION

The present invention relates to carbonate ionophores and carbonate sensors having membranes containing active amounts of these ionophores.

BACKGROUND OF THE INVENTION

Carbon dioxide, the major end product of the metabolism of foodstuffs, is the most commonly measured initial parameter in evaluating the body's ability to control pH. Carbonate ($CO_3^=$) and bicarbonate ($HCO_3^-$) anions in blood arise from dissolved carbon dioxide ($CO_2$). The relative amounts $CO_3^=$, $HCO_3^-$ and $CO_2$ are determined by equilibrium constants controlling the dissolution and dissociation of $CO_2$. This equilibrium system buffers blood, that is, it limits changes in blood pH that could occur upon entry of acid or base. Physiology controls the excretion of $CO_2$ through changes in the rate and depth of respiration. Knowledge of the $CO_3^=$, and therefore $CO_2$, concentration in the blood permits an approximation of the acid-base balance and aids in elucidating abnormal conditions. The measurement of the carbonate ion concentration in a blood, serum or plasma sample is a crucial test for clinical diagnosis.

Electrochemical sensor technology is an advantageous approach to measure the carbonate ion concentration in patient samples. Such technology is not subject to interferences that affect optically based technologies. A subset of electrochemistry is potentiometry, wherein the potential is measured at an ion-selective membrane interposed between a sample and a reference solution. Typically the ion-selective membrane comprises a polymer matrix, a plasticizer and an ionophore. The membrane so prepared captures the ions of interest in an amount proportional to the concentration of ion in the sample, produces a corresponding potential change and is assembled with appropriate electrical connections and reference solution to construct an ion-selective electrode (ISE). This ISE, together with a sample-contacting reference electrode, forms an electrochemical cell capable of measuring potentials that may be related to ion concentration in the sample.

A further development in ion-selective electrode technology is the solid-state sensor. A solid-state ISE does not utilize a solution-phase reference, reducing the size and complexity of the device. In addition, the design facilitates mass fabrication. Solid state sensor technology has been described in the patent literature, see for instance U.S. Pat. Nos. 5,522,978; 5,284,568; and 4,933,048.

Carbonate ionophores and carbonate sensor technology have been described in the scientific and patent literature. Early examples include *Analytical Chemistry* 41 (1969) 1128 and U.S. Pat. No. 3,723,281. Both of these possessed relatively low selectivity over chloride anion. Another example, *Analytica Chimica Acta* 76 (1975) 155, reported data demonstrating better selectivity over chloride, sulfate and phosphate, but utilized a liquid membrane, not a physically stable polymeric membrane. Meyerhoff and Greenberg report a carbonate-selective polymer membrane electrode in *Analytica Chimica Acta* 141 (1982) 57, but this sensor is subject to interference from salicylate anion, a metabolite of aspirin. Overcoming interference from salicylate is important for clinical applications.

U.S. Pat. No. 4,810,351 describes an ISE with improved selectivity for carbonate over salicylate, but the ISE is of the traditional configuration and requires an internal reference solution. U.S. Pat. No. 5,174,872 and *Clinical Chemistry* 32 (1986) 137 describe the addition of salicylate-complexing agents to samples in order to improve the apparent selectivity of carbonate ISEs. Additional approaches to overcoming salicylate interference include those described in *Analytical Chemistry* 65 (1993) 3151; U.S. Pat. No. 4,272,328; US statutory invention registration H745, and WO 9838503. Each of these constitutes a multilayered membrane structure or multilayered membrane with an internal filling solution, rendering the device more complex and less amenable to mass fabrication processes.

One of the major technical obstacles against commercialization of carbonate sensors is the lack of highly selective carbonate ionophores to overcome the interference of salicylate ion, a metabolite of commonly used drug aspirin. The present invention comprises a novel ionophore with improved selectivity of carbonate ions over salicylate ions. The major difference between the new ionophore and the previously known carbonate ionophores, such as described in *Analytica Chimica Acta* 233 (1990) 41, is the introduction of the amide group at the ortho-position of the benzene ring adjacent to the active site of the ionophore (trifluoroacetyl group). The amide group makes the trifluoroacetyl group (the active site for carbonate ion) not only more reactive, but also more sterically hindered. Enhancement of steric hindrance is thought to be desirable because the active site will be more selective to a smaller molecule, like a carbonate ion, than a larger molecule, such as salicylate ion. Such a selectivity improvement does not entail complex, multilayer membrane structures nor extensive sample pretreatment with additives. The disclosed ionophore is believed to be a novel and useful composition of matter.

SUMMARY OF THE INVENTION

It is an objective of this invention to provide novel ionophores for carbonate-selective electrodes possessing improved selectivity over salicylate, and other interfering anions. It is a further objective to describe the preparation of polymeric membranes containing the novel ionophores. Novel carbonate ionophores were synthesized and used in a solid-state sensor membrane to detect carbonate concentration in biological samples. The sensor membrane containing this novel ionophore demonstrated surprising selectivity for carbonate over other ions, especially for salicylate ion. Salicylate interference in clinical samples has been a major obstacle for developing a successful carbonate sensor. In addition, the sensor prepared with this ionophore has shown good use life, retaining at least 80% sensitivity.

The invention includes novel ionophores of the formula:

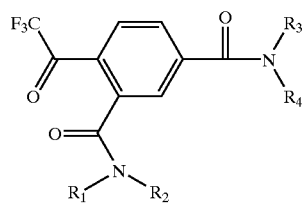

Formula 1 where $R_1$, $R_2$, $R_3$ and $R_4$ are independent straight or branched chain alkyl groups having 4 to 12 carbon atoms or the alkyl groups may optionally contain a cycloalkyl group having 3 to 8 carbon atoms or $R_1$ and $R_2$ or $R_3$ and $R_4$ together with N to which they are attached, can form a heterocycle ring having 5 to 8 carbon atoms.

In one embodiment, the compound depicted above is substituted at $R_1$, $R_2$, $R_3$, and $R_4$ with straight or branched chain alkyl groups having 4 to 12 carbon atoms.

In another embodiment, the compound depicted above is substituted at $R_1$, $R_2$, $R_3$ and $R_4$ with straight or branched chain alkyl groups having 6 to 10 carbon atoms.

In a most preferred embodiment, the compound depicted above is substituted at $R_1$, $R_2$, $R_3$, and $R_4$ with n-octyl groups.

Thus, the present invention includes sensors having a membrane with an ionophore for detecting carbonate ion in a test sample, the improvement comprising the addition of an effective amount of the above-described compound as the ionophore. Preferably, the ionophore for detecting carbonate is an effective amount of the compound depicted above as Formula 1 substituted at $R_1$, $R_2$, $R_3$, and $R_4$ with n-octyl groups. The term effective amount is intended to define the amount of ionophore required to provide good use life, retaining at least 80% sensitivity over a period from about two-weeks to about two months long.

DETAILED DESCRIPTION OF THE INVENTION

Several publications are referenced in this application. Full citation to those references is found where the publication is mentioned. Each of these publications is incorporated herein by reference. These publications relate to the art to which this invention pertains.

The current invention relates to novel compounds having the structure of Formula 1 wherein $R_1$, $R_2$, $R_3$ and $R_4$ are independently straight or branched chain alkyl groups having 4 to 12 carbon atoms or the alkyl groups may optionally contain a cycloalkyl group having 3 to 8 carbon atoms or $R_1$, $R_2$, $R_3$, and $R_4$ together with N to which they are attached, can form a heterocycle ring having 5 to 8 carbon atoms. Preferably, $R_1$, $R_2$, $R_3$, and $R_4$ are straight or branched chain alkyl having 4 to 12 carbon atoms, and more preferably having 6 to 10 carbon atoms. In one preferred embodiment $R_1$, $R_2$, $R_3$, and $R_4$ are n-octyl.

For use in a clinical environment, the novel class of compounds of this invention functions as an ionophore, defined as a compound that reacts with an analyte of interest, and is incorporated into carbonate-selective membranes that are components of solid-state sensors or ion-selective electrodes. General information regarding the composition and preparation of ion-selective membranes is found in Pace and Wang, U.S. Pat. No. 5,522,978, incorporated herein by reference. The membranes are composed of a polymer, plasticizer, a carbonate-selective ionophore, and an ion-exchanger. These constituents are dissolved in a suitable solvent, as described below, cast into membranes and dried by removal of solvent at ambient or elevated temperature. The percentages and ratios of the constituents given below reflect the composition of the dried membrane.

The polymer used for the membranes of the current invention can be selected from any material that imparts dimensionally stable characteristics suitable for handling and use of the membrane, whether the membrane is utilized in a solid-state sensor or in a conventional electrode incorporating an internal reference solution. A variety of polymers can be utilized including, but not limited to, poly (methyl methacrylate) and other acrylates, silicone rubbers, poly(carbonate), cellulose, cellulose ester, poly(vinyl acetate), poly(urethane), poly(vinyl butyral), poly(vinyl chloride), carboxylated poly(vinyl chloride), and other copolymers of vinyl chloride. By cellulose ester is meant all ester derivatives of cellulose including, but not limited to, cellulose acetate, cellulose butyrate, and other members of a homologous series. By poly(vinyl butyral) is meant a copolymer of vinyl butyral, vinyl, alcohol, and vinyl acetate. A mixture of approximately 1 part poly(vinyl chloride) to 4 parts poly(urethane) is preferred.

The amount of polymer material used is that amount sufficient to produce a membrane of suitable thickness and structural integrity for use as an ion-selective electrode of the present invention generally ranges between about 23 and 70% by weight. An amount of 36% by weight of total polymer in the dried membrane is preferred in this invention. The thickness of the carbonate-selective membrane of the present invention generally ranges from about $1\mu$ at to about $1000\ \mu$ in thickness and preferably about $50\ \mu$ in thickness.

The amount of the novel ionophore described by Formula 1 used in the membranes of the current invention is that amount sufficient to provide for the maximum selectivity of the membrane without altering or destroying the structural integrity of the membrane. The amount of ionophore can vary from about 5 to about 40 percent by weight. A concentration of 5 to 30 percent ion-selective agent is preferred.

Although the ionophore itself is an oil, a suitable amount of plasticizer enhances performance of the membrane. A variety of plasticizing agents may be utilized in the present invention, including but not limited to, bis(2-ethylhexyl) sebacate (DOS), bis(2-ethylhexyl) adipate (DOA), bis(2-ethylhexyl)phthalate, dicapryl adipate, dipentylphthalate (DPP), dibutylsebacate, tris(2-butoxyethyl)phosphate, tris (2-ethylhexyl)phosphate and 2-nitrophenyloctyl ether (NPOE). The amount of plasticizing agent used is that amount sufficient to maintain a solvated ion-selective membrane without destroying the selectivity or structural integrity of the membrane. The amount of plasticizing agent generally varies from about 25 to about 75 weight percent. A concentration of about 50 weight percent plasticizing agent is preferred.

In addition to the novel ionophore, the membrane may contain an ion-exchanger. The ion-exchanger reduces the effect of cationic interferences, as proposed in *Analytical Chemistry* 59 (1987) 144. Suitable ion-exchangers include, but are not limited to various quaternary ammonium salts, including, without limitation, tridodecylmethylammonium chloride (TDMAC), tridodecylmethylammonium carbonate, tricaprylmethylammonium chloride, tetraoctylammonium bromide, and tetraheptylammonium bromide. TDMAC is preferred for use in the membranes of the current invention. The amount of ion-exchanger agent used is that amount sufficient to provide for the maximum response of the carbonate sensor without altering or destroying selectivity for carbonate. The amount of ion-exchanger generally varies from about 1 to about 7 weight percent. A concentration of 1 weight percent ion-exchanger is preferred.

Other membrane components, such as fumed silica and silanes can be included in the carbonate-selective polymer membrane material, if desired, but such is not necessary to practice the present invention. The amount of fumed silica, if included, generally ranges from about 0 to about 15 weight percent. The amount of silane, if included, is that amount sufficient to provide adequate adhesion to a ceramic substrate or dielectric when the membrane is used in a planar sensor configuration. The amount of silane, if included, generally ranges from 0 to about 6 weight percent. In practicing this invention, a concentration of 0 to 4 weight percent of silane is preferred.

The carbonate-selective membrane of the electrode of the present invention can be prepared by mixing a suitable amount of polymer dissolved in an appropriate solvent with a suitable amounts of carbonate-selective ionophore, plasticizer and ion-exchanger to produce an ion-selective polymeric material. The solvent used can be any suitable solvent commonly used to prepare conventional membranes and can include, for example, isophorone, methylene choride, diethylene glycol monoethyl ether, tetrahydrofuran and cyclohexanone. In practicing this invention, isophorone is the preferred solvent.

Any order of mixing for the polymer material, carbonate-selective ionophore, ion-exchanger, silane and plasticizer can be used in preparing the ion-selective membrane of the present invention. Preferably, the polymer is dissolved in solvent. Fumed silica, if used, is added. Then ionophore, plasticizer, and ion-exchanger are added. The resulting carbonate-selective polymeric membrane material can be used to prepare carbonate-selective sensors in either the solid-state format or membrane-based electrodes in the conventional configuration with an internal reference solution. The production of either type of such electrodes can be achieved using known techniques and methodology. The carbonate-selective electrode of the present invention can be utilized with other ion-selective electrodes (ISEs) in multi-sensor assemblies.

The membrane of the current invention can be used as a component of an ion-selective electrode. These electrodes typically contain an internal filling solution, or electrolyte, and an internal reference electrode. A preferred reference electrode for the current invention is described in Lauks, U.S. Pat. No. 4,933,048, incorporated herein by reference.

Preferably, the electrodes containing membranes of the current invention are solid-state sensors. Solid-state sensors are smaller and easier to mass-produce than traditional electrodes. Solid state sensors are typically made by casting polymeric membranes on a solid surface, such as a metal conductor. Most preferably, the. membrane of the current invention is a component of a disposable cartridge, such as described in Pace and Hamerslag, U.S. Pat. No. 5,284,568, incorporated herein by reference. Cartridges of this type are preferably used in conjunction with the MultiPLY® or QuiikLYTE® cartridge for the Dimension® analyzer, *Clinical Chemistry* System (Dade Behring Inc., Deerfield, Ill.).

In the following examples, we synthesized a class of novel carbonate ionophores and membranes containing active amounts of these ionophores. These membranes were tested in the solid-state sensor format (Dimension® MultiPLY® or QuiikLYTE®) to detect carbonate concentration in biological samples. These carbonate ionophores, as well as membranes and sensors containing these ionophores are described in detail below. Example 1 describes the synthesis of 2,4-bis(N,N-dioctylamidyl), 1-trifluoroacetophenone (BDOTP). Example 2 describes synthesis of membranes containing BDOTP. Example 3 describes synthesis of membranes containing BDOTP. Example 4 demonstrates the carbonate selectivity of sensors containing membranes with BDOTP.

EXAMPLE 1

Synthesis of 2,4-Bis(N,N-dioctylamidyl), 1-trifluoroacetophenone (BDOTP)

In this Example, synthesis of 2,4-bis(N,N-dioctylamidyl), 1-trifluoroacetophenone (BDOTP) was carried out according to Scheme 1 below.

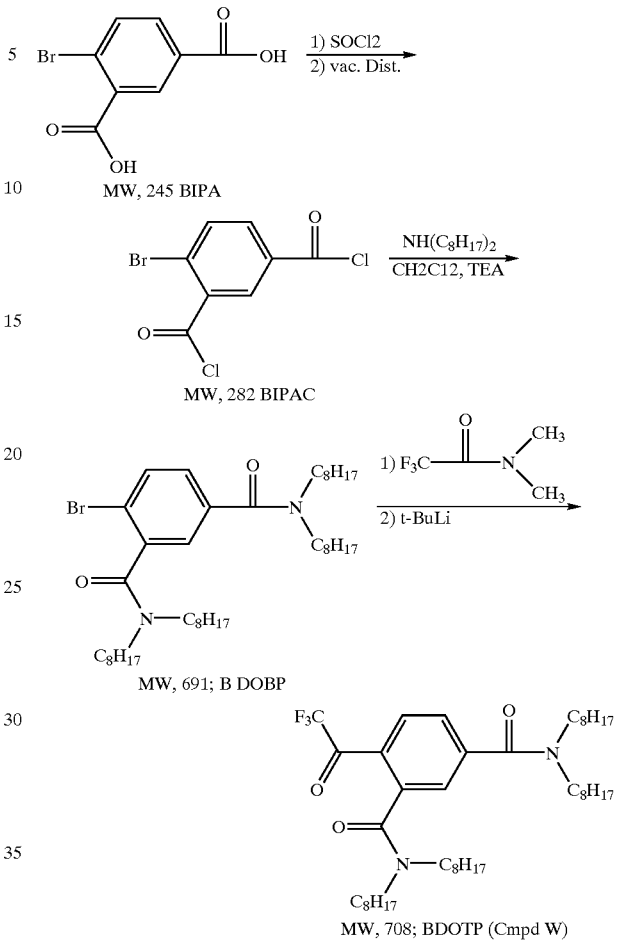

Bromo-isophthalic acid (BIPA) (15 g; 65 mmol) was refluxed with thionyl chloride (45 mL; 617 mmol) for 6 h until all solids were dissolved. Then the resultant bis(acid chloride) was purified by vacuum distillation (170° C./~2 Torr). The bis(acid chloride) (BIPAC) (15.71 g; 55 mmol) was cooled on ice bath and then allowed to react with dioctylamine (27.1 g; 112 mmol) in the presence of triethylamine (20.5 g; 203 mmol). Successive washes with aqueous sodium carbonate, water, 0.1 N HCl and water, followed by drying with sodium sulfate yielded a crude intermediate (BDOBP). Silica gel column chromatography with 80% hexane/20% EtOAc mixed solvents provided 39.3 g of clean BDOBP. The intermediate (BDOBP) reacted with dimethyltrifluoroaceamide in THF (450 ml) in the presence of t-butyl lithium (96.9 mL, 1.7 M pentane; 164.7 mmol) at −78° C. to yield BDOTP. The reaction was quenched with 0.1 N HCl, and followed with water wash. The organic solution was dried with sodium sulfate and removed by rotary evaporation. The product (BDOTP) was purified by chromatography on a silica gel column with 80% hexane/20% EtOAc mixed solvents. IR: 3265, 2956, 2857, 1726, 1643, 1466, 1427, 1378, 1204, 1150, 1114, 723 cm$^{-1}$. $^1$H-NMR (ppm, 400 MHz): 8.0 (t) 1H, 7.4–7.2(m) 2H, 3.5–3.0 (m) 8H, 1.8–1.1(m) 48H, 0.9(m) 12H. $^{19}$F-NMR (ppm, 400 MHz): 71.85.

EXAMPLE 2

Synthesis of Membranes Containing BDOTP

In this Example, membranes that incorporated BDOTP or Compound V (see Scheme 2) were synthesized. Synthesis of Compound V has been previously described by Behringer et al. (*Analytical Chimica Acta*, 233, 41–47 (1990)).

---

Scheme 2

Structures of Carbonate Ionophores.

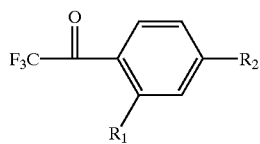

| Ionophore | MW (g/mol) | $R_1$ | $R_2$ |
|---|---|---|---|
| Compound V | 441.6 | H | —$CON(C_8H_{17})_2$ |
| BDOTP | 709.1 | —$CON(C_8H_{17})_2$ | —$CON(C_8H_{17})_2$ |

---

Membranes were prepared as follows: Dissolve 79.5 mg polyurethane (Thermedics Polymer Products, Product Number SG-80A) and 27.2 mg poly(vinyl chloride) (PVC) (Fluka Chemical Co., Product Number 81392) in 482.3 mg isophorone (Aldrich Chemical Co., Product Number W355505). Add 3 mg tridodecylmethylammonium chloride (TDMAC) (Aldrich Chemical Co., Product Number 36,772-9) and 160.5 mg bis(2-ethylhexyl)adipate ) (Fluka Chemical Co., Product Number 02138) and mix until homogeneous. Add 14.9 mg ionophore (BDOTP) and 12.0 mg silane crosslinking agent (3-glycidoxypropyltrimethyxysilane, Aldrich Chemical Co., Product Number 44-016-7). Pipet several microliters of the solution onto an insulated, Ag/AgCl-coated silver electrode. Allow to dry for 30 to 60 minutes at 70 degrees C. The dried membrane contained 5.0% (w/w) ionophore, 9.2% (w/w) PVC, 26.8% (w/w) polyurethane, 54.0% (w/w) bis(2-ethylhexyl)adipate, 4.0% (w/w) cross-linking agent, and 1.0% (w/w) tridodecylmethylammonium chloride (TDMAC). Electrochemical potentials for this electrode were measured relative to a Ag/AgCl reference electrode using a 0.1 M KCl liquid junction. The sensor yielded a slope of −19.3 mV/decade change in total $CO_2$ content when standardized against a conventional, Severinghaus $CO_2$ gas sensor. A 3 mM sodium salicylate spike introduced into a sample containing a background total $CO_2$ concentration of 15 mM evinced an increase of only 0.9 mM in the recovered total $CO_2$ concentration. In contrast, a sensor prepared using Compound V, yielded an increase of 19.4 mM recovered total $CO_2$ concentration for an identical salicylate spike.

EXAMPLE 3

Synthesis of Membranes Containing BDOTP

Dissolve 79.5 mg polyurethane (Thermedics Polymer Products, Product Number SG-80A) and 27.2 mg PVC ) (Fluka Chemical Co., Product Number 81392) in 482.3 mg isophorone isophorone (Aldrich Chemical Co., Product Number W355505). Add 3 mg TDMAC and 160.5 mg bis(2-ethylhexyl)adipate and mix until homogeneous. Add 14.9 mg ionophore (BDOTP) and 12.0 mg silane crosslinking agent (3-glycidoxypropyltrimethyxysilane, Aldrich Chemical Co., Product Number 44-016-7). Pipet several microliters of the solution onto an insulated, Ag/AgCl-coated silver electrode. Allow to dry for 30 to 60 minutes at 70 degrees C. The dried membrane contained 5.0% (w/w) ionophore, 26.8% (w/w) polyurethane, 9.2% (w/w) PVC, 54.0% (w/w) bis(2-ethylhexyl)adipate, 4.0% (w/w) cross-linking agent, and 1.0% (w/w) tridodecylmethylammonium chloride (TDMAC). Measure potential for this electrode relative to a Ag/AgCl reference electrode using a 0.1 M KCl liquid junction. The sensor yielded a slope of −22.1 mV/decade change in total $CO_2$ content when standardized against a conventional, Severinghaus $CO_2$ gas sensor. A 2.5 mM sodium salicylate spike introduced into a sample containing a background total $CO_2$ concentration of 18 mM evinced an increase of only 0.9 mM in the recovered total $CO_2$ concentration.

EXAMPLE 4

Demonstration of Carbonate Selectivity of Sensors Containing Membranes with BDOTP The sensor membrane cocktail was prepared similar to those in Examples 2 and 3 such that the non-solvent composition was 8.0% (w/w) ionophore (BDOTP), 30.0% w/w) polyurethane, 8.0% (w/w) PVC, 49.0% (w/w) bis(2-ethylhexyl)adipate and 1.2% (w/w) tridodecylmethylammonium chloride (TDMAC). For comparison, a membrane cocktail was prepared such that the non-solvent composition was 10.0% (w/w) ionophore (Compound V in Scheme 2 above), 24.0% (w/w) polyurethane, 8.5% (w/w) PVC, 51.0% (w/w) bis(2-ethylhexyl)adipate and 1.0% (w/w) TDMAC. Several microliters of the solution were dispensed onto an insulated, Ag/AgCl-coated silver electrode. The sensor was dried for 30 to 60 minutes at 70 degrees C. Potentials were measured relative to a Ag/AgCl reference electrode using a 0.1 M KCl liquid junction. The BDOTP-containing sensor yielded a slope of −29.7 mV/decade change in total $CO_2$ content when standardized against a conventional, Severinghaus $CO_2$ gas sensor. The same sensor yielded a slope of only −2.3 mV/decade change in sodium salicylate. In contrast, the Compound V-containing sensor yielded a slope of −30.8 mV/decade when used to measure total $CO_2$, but −20.3 mV/decade change in sodium salicylate.

The foregoing is intended to be illustrative of the present invention, but not limiting. Numerous variations and modifications of the present invention may be effected without departing from the true spirit and scope of the invention.

What is claimed is:

1. A compound of the formula:

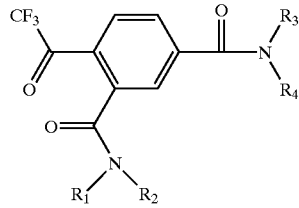

wherein $R_1$, $R_2$, $R_3$ and $R_4$ are independently straight or branched chain alkyl having 4 to 12 carbon atoms or the alkyl groups may optionally contain a cycloalkyl group having 3 to 8 carbon atoms or $R_1$ and $R_2$ or $R_3$ and $R_4$ together with N to which they are attached, can form a ring having 5 to 8 carbon atoms.

2. A compound according to claim 1 wherein $R_1$, $R_2$, $R_3$ and $R_4$ have 6 to 10 carbon atoms.

3. A sensor membrane comprising an effective amount of the compound of claim 2 as the ionophore.

4. A sensor comprising the membrane of claim 3.

5. A sensor for detecting carbonate comprising the membrane of claim 3.

6. A compound according to claim 1 wherein $R_1$, $R_2$, $R_3$, and $R_4$ are n-octyl.

7. A sensor membrane comprising an effective amount of the compound of claim 6 as the ionophore.

8. A sensor comprising the membrane of claim 7.

9. A sensor for detecting carbonate comprising the membrane of claim 7.

10. A sensor membrane comprising an effective amount of the compound of claim 1 as the ionophore.

11. A sensor comprising the membrane of claim 10.

12. A sensor for detecting carbonate comprising the membrane of claim 10.

* * * * *